United States Patent [19]

Schwartz

[11] 4,098,899

[45] Jul. 4, 1978

[54] METHOD OF REDUCING PSYCHOGENIC IMPOTENCE

[76] Inventor: George R. Schwartz, 301 Dartmouth N.E., Albuquerque, N. Mex.

[21] Appl. No.: 823,969

[22] Filed: Aug. 12, 1977

[51] Int. Cl.² ............................................. A61K 31/27
[52] U.S. Cl. .................................................. 424/300
[58] Field of Search ............................... 424/330, 300

[56] References Cited

PUBLICATIONS

Grollman, Pharmacology & Therapeutics, (1965), pp. 371–377.
Chem. Abst., vol. 76 – 108710q, (1972).
Chem. Abst., vol. 77 – 70819h (1972).

Primary Examiner—Stanley J. Friedman
Attorney, Agent, or Firm—Max R. Millman

[57] ABSTRACT

A method of reducing psychogenic impotence by ingestion of neostigmine bromide or neostigmine methyl sulfate at a time prior to sexual attempt and in an amount sufficient to produce sensual stimulation. Administration by oral mucosal absorption, i.e. sub-lingually enhances the effect of the medication.

5 Claims, No Drawings

METHOD OF REDUCING PSYCHOGENIC IMPOTENCE

This invention relates neostigmine bromide or neostigmine methyl sulfate as a pharmaceutical agent to reduce psychogenic impotence in physiologically normal men.

Men who are physiologically normal by all available tests but who fail to achieve erections in most of their attempts have been treated almost exclusively by psychological means with relatively small success. Such erectile impotence has long been observed to have a significant association with worry and anxiety.

It is the primary object of this invention to provide a pharmaceutical treatment for psychological or psychogenic impotence.

Neostigmine bromide or neostigmine methyl sulfate which is available commercially as Prostigmin bromide or Prostigmin methyl sulfate from Roche Pharmaceutical Co. stimulates the parasympathetic nervous system. It inhibits the destruction of acetylcholine by inhibiting or inactivating acetylcholinerase, the enzyme which normally destroys naturally formed and released acetylcholine; thereby, neostigmine bromide allows additional cholinergic stimulation. Thus, neostigmine bromide causes acetylcholine to accumulate and to exert a longer stimulatory action at sensitive sites throughout the nervous system.

For this reason, the principal use of neostigmine bromide is in the treatment of Myasthenia Gravis whose basic symptom is muscular weakness which results from a reduction in the amount of acetylcholine available at the nerve-muscle junction. It is the acetylcholine which causes the muscle to respond by contraction. In Myasthenia Gravis, neostigmine bromide seems also to act directly on the muscle membrane, thereby enhancing muscular strength. The aerage daily dose of neostigmine bromide in the treatment of Myasthenia Gravis is 150 mg (ten 15 mg tablets). Some patients receive as much as 400 mg neostigmine bromide daily.

The actions of the sympathetic and parasympathetic nervous systems are opposed. The sympathetic nervous system seems to prepare the body for nervous or vigorous muscular activity and has therefore been called the system of "flight or fight"; whereas the parasympathetic nervous system acts more discretely on individual organs or regions of the body and has therefore been called the "housekeeper" of the body, regulating ordinary functions of living (digestion, urine flow, etc.). Accordingly, the integrating activity of the autonomic nervous system (sympathetic and parasympathetic) is of vital importance for the well being of the organism.

Applicant believes that neostigmine bromide is a balancing agent for these two opposed systems because of its cholinergic stimulating effect on the parasympathetic nervous system. While neostigmine bromide has been used for paralytic ileus and atony of the urinary bladder, glaucoma and some other eye conditions, and atropine intoxication as reported in "The Pharmacological Basis of Therapeutics" by Goodman and Gilman (1975 Ed.) Macmillan & Company, applicant has discovered that in relatively small doses and by oral mucosal absorption, neostigmine bromide is very effective in reducing psychological or psychogenic impotence in men.

Applicant is aware that neostigmine bromide has been used intrathecally, i.e. by injection into the part of the back associated with outflow of nerves to the genitalia from the spinal cord, in cord-injured patients to produce ejaculation generally with erection, Guttman and Walsh: "Prostigmin Assessment Test of Fertility in Spinal Man", Paraplegia 9:39-51, 1971 and Griffith. Tomko and Timms, "Sexual Function in Spinal Cord-Injured Patients: A Review" Arch. Phys. Med. Rehabil. Vol. 54, pp. 539-543, Dec. 1973.

However, it is applicant who has discovered the effectiveness of neostigmine bromide on physiologically normal but psychologically impotent men especially when administered by oral mucosal absorption, i.e. sub-lingually.

A number of men were treated with neostigmine bromide in accordance with the instant invention and the results obtained are shown in the following Table 1. All men treated had an essentially normal physical examination and were not taking any other drugs or medicines, aside from coffee or tea. Blood flow to their genitals was clinically adequate and all had been previously diagnosed as "psychologically" impotent.

Table 1

| Patient | Age | Phys. Exam. | Dosage Used | Results |
|---|---|---|---|---|
| 1 | 33 | Normal | 15 mg | Definite improvement, 50% impotent before, 100% potent after |
| 2 | 42 | Normal | 30 mg | Definite improvement, <50% potent before, 80% potent after |
| 3 | 48 | Hypertensive | 30 mg | Improvement, but not consistent |
| 4 | 24 | Normal | 15 mg | Definite improvement, from sex avoidance to 100% success |

Patient 1 with previously good sexual functioning was experiencing loss of erectile ability, although his desire was still present but diminished. The physical examination and laboratory tests including the SMA-12 (a conventional screening test of 12 body functions) were normal. This same SMA-12 screening test was used on all four patients. Patient 1 reported that he was under stress at his job and had recently been divorced after a stormy marriage. He had seen a psychiatrist for five visits and not only noticed no improvement in his ability to attain erection, but also found that after each psychiatric session his ability to achieve erection was further diminished. He was given neostigmine bromide one hour prior to any sexual attempt. He was told to "swill" the tablet in his mouth for ten minutes before swallowing. His results were dramatic. He reported that he could feel the effects of the drug in that his stomach "gurgled" more, and he felt a bit "sweaty". After two weeks of almost daily sexual intercourse, he stopped using the drug and no longer required it except in unusual situations of a stressful day or particular worries.

Patient 2 was married 20 years, had a daughter aged 18 and was an insurance salesman. Patient 3 was married twice and had children by the first marriage and no problem in the first marriage. Patient 4 was unmarried, feared that he was a homosexual but had a girlfriend.

All four patients reported a substantial heightening of their erectile ability. None required more than two 15 mg tablets. When the medication was discontinued, an apparently lasting change had occurred in that all found it easier subsequently to achieve erection without any pharmacological aid.

A clinical test was carried out as to the route of administration of the neostigmine bromide. One patient was instructed to either swallow the two 15 mg tablets or to swill them in his mouth for about 20 minutes. He did this five times and the first time the tablets were being swilled he described the effects. The eventual effects were felt to be stronger when the tablets were first swilled and then swallowed and the effects more rapid. The experiment was carried out on ten different days with at least one day intervening between tests to avoid problems of an existent drug level which could be accentuated. Thus, oral absorption was more effective than swallowing. In addition, a feeling of sleepiness and of calm was associated with swilling first, with similar but diminished effect if the tablets were merely swallowed.

An additional experiment was conducted on a male aged 32 who had taken no prior medication. The subject ingested on the following days either 30 mg neostigmine bromide or two placebo tablets of lactose wrapped in tin foil and ingested blindfolded on each occasion. Neither the experimenter nor the subject knew which medication was ingested. The medication was administered every 3 days to allow time between trials. The subject was asked to respond to the following questions 45 minutes after each ingestion: (1) alert or drowsy, (2) ease of entering meditative (relaxed) state as compared to usual, (3) feeling of bowel action or salvation, (4) erection or sensual stimulation, and (5) feeling of or need to urinate.

The results are set forth in the following Table 2.

Table 2

| Drug | Day | Alert/Drowsy | (Meditation Relaxation) | Bowel | Spontaneous Erection | Bladder |
|---|---|---|---|---|---|---|
| N | 1 | D | Easier | + | 0 | + |
| N | 4 | D | Easier | + | + | + |
| P | 7 | D | Same | 0 | 0 | 0 |
| N | 10 | D | Easier | + | + | + |
| P | 13 | — | Same | 0 | 0 | + |
| N | 16 | D | Easier | + | 0 | + |
| P | 19 | D | Hard | + | 0 | 0 |
| N | 22 | D | Easier | + | 0 | + |

P = placebo.
N = neostigmine bromide

Recap Table

| | Alert | Drowsy | (Meditation) Easier | Hard | Same | Bowel | Erect | Bladder |
|---|---|---|---|---|---|---|---|---|
| P (3 trials) | 1 | 2 | 0 | 1 | 2 | 1/3 | 0/3 | 1/3 |
| N (5 trials) | 0 | 5 | 5 | 0 | 0 | 5/5 | 2/5 | 5/5 |

Yet another test was carried out on a subject five different days in which he was given either two 15 mg tablets of neostigmine bromide or two aspirin tablets one hour prior to sleep. He reported that sleep came more easily on each occasion, that he felt calmer, more thoughtful and less attentive to external sensory events indicating an observable effect on the central nervous system, that swallowing was a little more difficult and that he felt more stomach and intestinal activity. He reported that he also felt that his strength increased, he noted a slight tendency to stare and relax his eye muscles and that he felt more tranquil. A relaxation response appeared to be facilitated.

Thus, it has been discovered that administering neostigmine bromide or neostigmine methyl sulfate in relatively small doses of 15 mg or 30 mg without one hour prior to sexual attempt, especially when administered by swilling or oral mucosal absorption (sub-lingually) has a significant affect on diminishing psychological impotence. In the sub-lingual administration, the neostigmine bromide takes effect in 8-10 minutes. Since it increases the parasympathetic tone by cholinergic stimulation and since older people may produce too little choline, administration of neostigmine bromide may enhance the sexuality in older people.

What is claimed is:

1. A method of reducing psychological impotence in man comprising administering to a psychologically impotent man by oral ingestion a cholinergic stimulant in a dosage and at a time prior to sexual attempt sufficient to product sensual stimulation, said stimulant being selected from the group consisting of neostigmine bromide and neostigmine methyl sulfate.

2. The method of claim 1 wherein the compound is neostigmine bromide and the dosage is a minimum of 15 mg and a maximum of 30 mg.

3. The method of claim 2 wherein the oral ingestion administration is effected by swilling the neostigmine bromide in the mouth.

4. The method of claim 3 wherein the neostigmine bromide is administered about one hour prior to sexual attempt.

5. A method of reducing psychological impotence in a man comprising placing in the mouth of a psychologically impotent man a minimum of 15mg. and a maximum of 30mg. of neostigmine bromide about one hour before a sexual attempt and swilling the compound until it is absorbed by the oral mucosa.

* * * * *

UNITED STATES PATENT OFFICE
CERTIFICATE OF CORRECTION

Patent No. 4,098,899  Dated July 4, 1978

Inventor(s) George R. Schwartz

It is certified that error appears in the above-identified patent and that said Letters Patent are hereby corrected as shown below:

Col. 1, line 38, "aerage" should be ---average---.

Col. 4, line 12, "without" should be ---within---.

*Signed and Sealed this*

*Fifteenth* Day of *January 1980*

[SEAL]

*Attest:*

SIDNEY A. DIAMOND

*Attesting Officer*  *Commissioner of Patents and Trademarks*